United States Patent [19]
Oakes et al.

[11] Patent Number: 5,718,910
[45] Date of Patent: Feb. 17, 1998

[54] PEROXYACID ANTIMICROBIAL COMPOSITION

[75] Inventors: Thomas R. Oakes, Lake Elmo; Patricia M. Stanley, Minneapolis; Jerome D. Keller, Eagan, all of Minn.

[73] Assignee: Ecolab Inc., St. Paul, Minn.

[21] Appl. No.: 4,075

[22] Filed: Jan. 13, 1993

Related U.S. Application Data

[62] Division of Ser. No. 734,580, Jul. 23, 1991, Pat. No. 5,200,189.

[51] Int. Cl.$^6$ .................................................. A01N 25/02
[52] U.S. Cl. ..................... 424/405; 514/557; 514/558; 514/559; 514/714
[58] Field of Search ................... 424/405; 514/557–559, 514/714

[56] References Cited

U.S. PATENT DOCUMENTS

| | | | |
|---|---|---|---|
| 3,248,281 | 4/1966 | Goodenough | 167/17 |
| 3,350,265 | 10/1967 | Rubinstein et al. | 167/38.6 |
| 3,514,278 | 5/1970 | Brink, Jr. | 71/67 |
| 3,895,116 | 7/1975 | Herting et al. | 424/317 |
| 4,041,149 | 8/1977 | Gaffar et al. | 424/57 |
| 4,370,199 | 1/1983 | Orndorff | 162/161 |
| 4,404,040 | 9/1983 | Wang | 134/22.14 |
| 4,477,438 | 10/1984 | Willcockson et al. | 424/130 |
| 4,478,683 | 10/1984 | Orndorff | 162/161 |
| 4,592,488 | 6/1986 | Simon et al. | 222/94 |
| 4,738,840 | 4/1988 | Simon et al. | 424/51 |
| 4,802,994 | 2/1989 | Mouche et al. | 210/759 |
| 4,865,752 | 9/1989 | Jacobs | 210/791 |
| 4,917,815 | 4/1990 | Beilfuss et al. | 252/186.23 |
| 4,923,677 | 5/1990 | Simon et al. | 422/37 |
| 4,937,066 | 6/1990 | Vlock | 424/52 |
| 4,943,414 | 7/1990 | Jacobs et al. | 422/28 |
| 4,996,062 | 2/1991 | Lehtonen et al. | 426/8 |
| 4,997,571 | 3/1991 | Roensch et al. | 210/698 |
| 4,997,625 | 3/1991 | Simon et al. | 422/29 |
| 5,010,109 | 4/1991 | Inoi | 514/714 |
| 5,015,408 | 5/1991 | Reuss | 252/99 |
| 5,043,176 | 8/1991 | Bycroft et al. | 426/335 |
| 5,069,286 | 12/1991 | Roensch et al. | 166/312 |
| 5,084,239 | 1/1992 | Moulton et al. | 422/22 |
| 5,114,718 | 5/1992 | Damani | 424/422 |
| 5,122,538 | 6/1992 | Lokkesmoe et al. | 514/557 |
| 5,129,824 | 7/1992 | Keller | 433/215 |
| 5,130,124 | 7/1992 | Merianos et al. | 424/53 |
| 5,139,788 | 8/1992 | Schmidt | 424/616 |
| 5,176,899 | 1/1993 | Montgomery | 424/50 |
| 5,200,189 | 4/1993 | Oakes et al. | 424/405 |

FOREIGN PATENT DOCUMENTS 0233731  8/1987  European Pat. Off.

*Primary Examiner*—Neil Levy
*Attorney, Agent, or Firm*—Merchant, Gould, Smith, Edell, Welter & Schmidt, P.A.

[57] ABSTRACT

A peroxyacid antimicrobial concentrate and use composition is provided comprising a $C_1$ to $C_4$ peroxycarboxylic acid, and a $C_6$ to $C_{18}$ peroxyacid. The combination of these acids produces a synergistic effect, providing a much more potent biocide than can be obtained by using these components separately. Other components can be added to the composition such as hydrotrope coupling agents, stabilizers, etc. An effective antimicrobial use solution is formed at low concentrations when the concentrate composition is diluted with water to a pH in the range of about 2 to 8. Sanitizing of substantially fixed, "in-place" processing lines in dairies, breweries, and other food processing operations is one utility of the composition.

32 Claims, No Drawings

PEROXYACID ANTIMICROBIAL COMPOSITION

This is a division, of application Ser. No. 07/734,580, filed Jul. 23, 1991 U.S. Pat. No. 5,200,189.

FIELD OF THE INVENTION

The invention relates generally to antimicrobial or biocidal compositions. More particularly, the invention relates to peroxyacid antimicrobial concentrates and use solutions which can sanitize various surfaces such as facilities and equipment found in the food processing and food service industries, and various inanimate surfaces in the health care industry.

BACKGROUND OF THE INVENTION

Numerous classes of chemical compounds exhibit varying degrees of antimicrobial or biocidal activity. Antimicrobial compositions are particularly needed in the food and beverage industries to clean and sanitize processing facilities such as pipelines, tanks, mixers, etc. and continuously operating homogenation or pasteurization apparatus. Sanitizing compositions have been formulated in the past to combat microbial growth in such facilities. For example, Wang, U.S. Pat. No. 4,404,040, teaches a short chain fatty acid sanitizing composition comprising an aliphatic short chain fatty acid, a hydrotrope solubilizer capable of solubilizing the fatty acid in both the concentrate and use solution, and a hydrotrope compatible acid so that the use solution has a pH in the range of 2.0 to 5.0.

Peroxy-containing compositions are known for use in the production of microbicidal agents. One such composition is disclosed in Bowing et al., U.S. Pat. No. 4,051,059 containing peracetic acid, acetic acid or mixtures of peracetic and acetic acid, hydrogen peroxide, anionic surface active compounds such as sulfonates and sulfates, and water Peracetic acid has been shown to be a good biocide, but only at fairly high concentrations (generally greater than 100 part per million (ppm)). Similarly, peroxyfatty acids have also been shown to be biocidal, but only at high concentrations (greater than 200 ppm), such as in the composition disclosed in European Patent Application No. 233,731.

Antimicrobial compositions having low use concentrations (less than 100 ppm) which effectively kill microbes are particularly desirable. Low concentrations minimize use cost, surface corrosion, odor, carryover of biocide into foods and potential toxic effects to the user. Therefore, a continuing need exists to provide such an antimicrobial composition for use in food processing, food service and health care facilities. In contrast to the prior art, the composition of the present invention has the unique advantage of having antimicrobial or biocidal activity at low level use concentrations.

SUMMARY OF THE INVENTION

The invention is a peroxyacid antimicrobial concentrate and diluted end use composition comprising an effective microbicidal amount of a $C_1$–$C_4$ peroxycarboxylic acid, and an effective microbicidal amount of a $C_6$–$C_{18}$ peroxyacid. The concentrate composition can be diluted with a major proportion of water to form an antimicrobial sanitizing-use solution having a pH in the range of about 2 to 8, with a $C_1$–$C_4$ peroxycarboxylic acid concentration of at least about 10 ppm, preferably about 10 to 75 ppm, and a $C_6$–$C_{18}$ peroxyacid concentration of at least about 1 ppm, preferably about 1 to 25 ppm. Other components may be added such as a hydrotrope coupling agent for solubilizing the peroxyfatty acid in the concentrate form and when the concentrate composition is diluted with water.

In contrast to the prior art, we have discovered that at a low pH, (e.g. preferably less than 5) $C_6$–$C_{18}$ peroxyacids such as peroxyfatty acids are very potent biocides at low levels. When used in combination with a $C_1$–$C_4$ peroxycarboxylic acid such as peroxyacetic acid, a synergistic effect is obtained, providing a much more potent biocide than can be obtained by using these components separately. This means that substantially lower concentrations of biocide can be used to obtain equal cidal effects, leading to lower costs of the product and less potential for corrosion.

As the term is used herein, a $C_6$–$C_{18}$ peroxyacid (or peracid) is intended to mean the product of the oxidation of a $C_6$–$C_{18}$ acid such as a fatty acid, or a mixture of acids, to form a peroxyacid having from about 6 to 18 carbon atoms per molecule. The $C_1$–$C_4$ peroxycarboxylic acid is intended to mean the product of oxidation of a $C_1$–$C_4$ carboxylic acid, or a mixture thereof. This includes both simple and substituted $C_1$–$C_4$ carboxylic acids.

A method of sanitizing facilities or equipment comprises the steps of contacting the facilities or equipment with the use solution made from the above concentrate composition of the invention at a temperature in the range of about 4° to 60° C. The composition is then circulated or left in contact with the facilities or equipment for a time sufficient to sanitize (generally at least 30 seconds) and the composition is thereafter drained or removed from the facilities or equipment.

One aspect of the invention is the novel, antimicrobial concentrate composition which is capable of being diluted with a major proportion of water to form a sanitizing use solution. A further aspect of the invention is an aqueous antimicrobial sanitizing use solution which is particularly suited for "in-place" cleaning applications. A further aspect of the invention is a method of employing the use solution of the invention in the cleaning or satirizing of various process facilities or equipment as well as other surfaces.

DETAILED DESCRIPTION OF THE INVENTION

The invention resides in a peroxyacid antimicrobial concentrate and use composition comprising an effective microbicidal amount of a $C_1$–$C_4$ peroxycarboxylic acid, and an effective microbicidal amount of a $C_6$–$C_{18}$ peroxyacid. We have found that combining these acids produces a synergistic effect, producing a much more potent biocide than can be obtained by using these components separately. The concentrate composition can be diluted with a major proportion of water to form an antimicrobial sanitizing use solution having a pH in the range of about 2 to 8. The sanitizing use solution can be used effectively to clean or sanitize facilities and equipment used in thé food processing, food service and health care industries.

Peracids

The present invention is based upon the surprising discovery that when a $C_6$–$C_{18}$ peroxyacid is combined with a $C_1$–$C_4$ peroxycarboxylic acid, a synergistic effect is produced and greatly enhanced antimicrobial activity is exhibited when compared to the $C_6$–$C_{18}$ peroxyacid or the $C_1$–$C_4$ peroxycarboxylic acid alone. The present blend of a $C_6$–$C_{18}$ peroxyacid and a $C_1$–$C_4$ peroxycarhoxylic acid can effectively kill microorganisms (e.g., a 5 $\log_{10}$ reduction in 30 seconds) from a concentration level below 100 ppm and as low as 20 ppm of the peracid blend.

A variety of $C_6$–$C_{18}$ peroxyacids may be employed in the composition of the invention such as peroxyfatty acids, monoperoxy- or diperoxydicarboxylic acids, and peroxyaromatic acids. The $C_6$–$C_{18}$ peroxyacids employed in the present invention may be structurally represented as follows: $R_1$—$CO_3H$, wherein $R_1$ is a hydrocarbon moiety having from about 5 to 17 carbon atoms (a $C_8$ peroxyacid is generally represented structurally as $C_7$—$CO_3H$). $R_1$ may have substituents in the chain, e.g., —OH, $CO_2H$, or heteroatoms (e.g., —O— as in alkylether carboxylic acids), as long as the antimicrobial properties of the overall composition are not significantly affected. It should be recognized that "$R_1$" substituents or heteroatoms may change the overall acidity (i.e., pKa) of the carboxylic acids herein described. Such modification is within the contemplation of the present invention provided the advantageous antimicrobial performance is maintained. Furthermore, $R_1$ may be linear, branched, cyclic or aromatic. Preferred hydrocarbon moieties (i.e. preferred $R_1$'s) include linear, saturated, hydrocarbon aliphatic moieties having from 7 to 11 carbon atoms (or 8 to 12 carbon atoms per molecule).

Specific examples of suitable $C_6$–$C_{18}$ carboxylic fatty acids which can be reacted with hydrogen peroxide to form peroxyfatty acids include such saturated fatty acids as hexanoic ($C_6$), enanthic (heptanoic) ($C_7$), caprylic (octanoic) ($C_8$), pelargonic (nonanoic) ($C_9$), capric (decanoic) ($C_{10}$), undecyclic (undecanoic) ($C_{11}$), lauric (dodecanoic) ($C_{12}$), tridecylic (tridecanoic) ($C_{13}$), myristic (tetradecanoic) ($C_{14}$), palmitic (hexadecanoic) ($C_{16}$), and stearic (octodecanoic) ($C_{18}$). These acids can be derived from both natural and synthetic sources. Natural sources include animal and vegetable fats or oils which should be fully hydrogenated. Synthetic acids can be produced by the oxidation of petroleum wax. Particularly preferred peroxyfatty acids for use in the composition of the invention are linear monoperoxy aliphatic fatty acids such as peroxyoctanoic acid, peroxydecanoic acid, or mixtures thereof.

Other suitable $C_6$–$C_{18}$ peroxyacids are derived from the oxidation of dicarboxylic acids and aromatic acids. Suitable dicarboxylic acids include adipic acid ($C_6$) and sebacic acid ($C_{10}$). An example of a suitable aromatic acid is benzoic acid. These acids can be reacted with hydrogen peroxide to form the peracid form suitable for use in the composition of the invention. Preferred peracids in this group include monoperoxy- or diperoxyadipic acid, monoperoxy- or diperoxysebacic acid, and peroxybenzoic acid.

The above peroxyacids provide antibacterial activity against a wide variety of microorganisms, such as gram positive (e.g., *Staphylococcus aureus*) and gram negative (e.g., *Escherichia coli*) microorganisms, yeast, molds, bacterial spores, etc. When the above $C_6$–$C_{18}$ peroxyacids are combined with a $C_1$–$C_4$ peroxycarboxylic acid, greatly enhanced activity is shown compared to the $C_1$–$C_4$ peroxycarboxylic acid alone or the $C_6$–$C_{18}$ peroxyacid alone.

The $C_1$–$C_4$ peroxycarboxylic acid component can be derived from a $C_1$–$C_4$ carboxylic acid or dicarboxylic acid by reacting the acid with hydrogen peroxide. Examples of suitable $C_1$–$C_4$ carboxylic acids include acetic acid, propionic acid, glycolic acid, and succinic acid. Preferable $C_1$–$C_4$ peroxycarboxylic acids for use in the composition of the invention include peroxyacetic acid, peroxypropionic acid, peroxyglycolic acid, peroxysuccinic acid, or mixtures thereof.

The antimicrobial concentrate of the present invention can comprise about 0.01 to 10 wt-%, preferably about 0.05 to 5 wt-%, and most preferably about 0.1 to 2 wt-% of a $C_6$–$C_{18}$ peroxyacid, and about 0.1 to 25 wt-%, preferably about 0.5 to 20 wt-%, and most preferably about 1 to 15 wt-% of a $C_1$–$C_4$ peroxycarboxylic acid. The concentrate composition preferably has a weight ratio of $C_1$–$C_4$ peroxycarboxylic acid to $C_6$–$C_{18}$ peroxyacid of about 15:1 to 3:1. The concentrate contains sufficient acid so that the end use solution has a pH of about 2 to 8, preferably about 3 to 7. Some acidity may come from an inert acidulant which may be optionally added (e.g., phosphoric acid).

The peracid components used in the composition of the invention can be produced in a simple manner by mixing a hydrogen peroxide ($H_2O_2$) solution with the desired amount of acid. With the higher molecular weight fatty acids, a hydrotrope coupler may be required to help solubilize the fatty acid. The $H_2O_2$ solution also can be added to previously made peracids such as peracetic acid or various perfatty acids to produce the peracid composition of the invention. The concentrate can contain about 1 to 50 wt-%, preferably about 5 to 25 wt-% of hydrogen peroxide.

The concentrate composition can further comprise a free $C_6$–$C_{18}$ carboxylic acid, a free $C_1$–$C_4$ carboxylic acid, or mixtures thereof. The free acids will preferably correspond to the starting materials used in the preparation of the peroxyacid components. The free $C_6$–$C_{18}$ carboxylic acid is preferably linear and saturated, has 8 to 12 carbon atoms per molecule, and can also comprise a mixture of acids. The free $C_6$–$C_{18}$ carboxylic acid and free $C_1$–$C_4$ carboxylic acid can be present as a result of an equilibrium reaction with the hydrogen peroxide to form the peroxyacids.

Optional Components

Various optional materials may be added to the composition of the invention to help solubilize the fatty acids, restrict or enhance the formation of foam, to control hard water, to stabilize the composition, or to further enhance the antimicrobial activity of the composition.

The composition of the invention can contain a surfactant hydrotrope coupling agent or solubilizer that permits blending short chain perfatty acids in aqueous liquids. Functionally speaking, the suitable couplers which can be employed are non-toxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters) and $C_8$–$C_{10}$ alkyl glucosides. Preferred coupling agents for use in the present invention include noctanesulfonate, available as NAS 8D from Ecolab, and the commonly available aromatic sulfonates such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

The hydrotrope coupling agent can comprise about 0.1 to 30 wt-%, preferably about 1 to 20 wt-%, and most preferably about 2 to 15 wt-% of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition, particularly in cold or soft water. A particularly useful nonionic surfactant for use as a defoamer is nonylphenol having an average of 12 moles of ethylene oxide condensed thereon, it being encapped with a hydrophobic portion comprising an average of 30 moles of propylene oxide.

Chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST" has been found to be effective. Chelating agents can be added to the present composition to control or sequester hardness ions such as calcium and magnesium. this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The composition of the invention can be made by combining by simple mixing an effective amount of a $C_6$–$C_{18}$ peroxyacid such as a peroxyfatty acid with some source of a $C_1$–$C_4$ peroxycarboxylic acid such as peroxyacetic acid. This composition would be formulated with preformed perfatty acid and preformed peroxyacetic acid. A preferred composition of the invention can be made by mixing a $C_1$–$C_4$ carboxylic acid, a $C_6$–$C_{18}$ carboxylic acid, a coupler and a stabilizer and reacting this mixture with hydrogen peroxide. A stable equilibrium mixture is produced containing a $C_1$–$C_4$ peroxycarboxylic acid and a $C_6$–$C_{18}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, a $C_1$–$C_4$ carboxylic acid, a $C_6$–$C_{18}$ carboxylic acid, a $C_1$–$C_4$ peroxycarboxylic acid, a $C_6$–$C_{18}$ peroxyacid, water, and various couplers and stabilizers.

By using the above approach, the composition of the invention can be formulated by merely mixing readily available raw materials, e.g., acetic acid, hydrogen peroxide and fatty acid. By allowing solution time for equilibrium to be obtained, the product containing both of the active biocides is obtained. In varying the ratio of $C_1$–$C_4$ carboxylic acid to $C_6$–$C_{18}$ carboxylic acid, it is easy to vary the ratio of $C_1$–$C_4$ peroxycarboxylic acid to $C_6$–$C_{18}$ peroxyacid.

Concentrate and Use Compositions

The present invention contemplates a concentrate composition which is diluted to a use solution prior to its utilization as a sanitizer. Primarily for reasons of economics, the concentrate would normally be marketed and the end user would dilute the concentrate with water to a use solution. A preferred antimicrobial concentrate composition comprises about 0.01 to 10 wt-%, preferably about 0.05 to 5 wt-%, of a $C_6$–$C_{18}$ peroxyfatty acid, about 0.1 to 25 wt-%, preferably about 0.5 to 20 wt-%, of a $C_1$–$C_4$ peroxycarboxylic acid, about 0.1 to 30 wt-% of a hydrotrope coupling agent, and about 1 to 50 wt-% of hydrogen peroxide. Other acidulants may optionally be employed in the composition such as phosphoric acid.

The level of active components in the concentrate composition is dependent upon the intended dilution factor and desired acidity in the use solution. The $C_6$–$C_{18}$ peroxyacid component is generally obtained by reacting a $C_6$–$C_{18}$ carboxylic acid with hydrogen peroxide in the presence of a $C_1$–$C_4$ carboxylic acid. The resulting concentrate is diluted with water to provide the use solution. Generally, a dilution of 1 fluid oz. to 4 gallons (i.e. dilution of 1 to 500 by volume) or to 8 gallons (i.e. dilution of 1 to 1,000 by volume) of water can be obtained with 2% to 20% total peracids in the concentrate. Higher use dilution can be employed if elevated use temperature (greater than 20° C.) or extended exposure time (greater than 30 seconds) are also employed.

In its intended end use, the concentrate is diluted with a major proportion of water and used for purposes of sanitization. The typical concentrate composition described above is diluted with available tap or service water to a formulation of approximately 1 oz. concentrate to 8 gallons of water. An aqueous antimicrobial sanitizing use solution comprises at least about 1 part per million (ppm), preferably about 2 to 10 ppm of a $C_6$–$C_{18}$ peroxyacid, and at least about 10 ppm, preferably about 20 to 50 ppm of a $C_1$–$C_4$ peroxycarboxylic acid. The weight ratio of $C_6$–$C_{18}$ peroxyacid to $C_1$–$C_4$ peroxycarboxylic acid ranges from about 0.01 to 0.5 parts, preferably about 0.02 to 0.2 parts of $C_6$–$C_{18}$ peroxyacid per part of $C_1$–$C_4$ peroxycarboxylic acid. Preferably the total peracid concentration in the use solution is less than about 75 ppm, and most preferably between about 5 to 50 ppm. Higher levels of peracids can be employed in the use solution to obtain disinfecting or sterilizing results.

The aqueous use solution can further comprise at least about 1 ppm, preferably about 2 to 20 ppm, of a hydrotrope coupling agent, at least about 1 ppm, preferably about 2 to 200 ppm of hydrogen peroxide, and at least about 1 ppm, preferably about 2 to 200 ppm of a free $C_6$–$C_{18}$ carboxylic acid, a free $C_1$–$C_4$ carboxylic acid, or mixtures thereof. The aqueous use solution has a pH in the range of about 2 to 8, preferably about 3 to 7.

Methods of Use

As noted above, the present composition is useful in the cleaning or sanitizing of processing facilities or equipment in the food service, food processing or health care industries.

Examples of process facilities in which the composition of the invention can be employed include a milk line dairy, a continuous brewing system, food processing lines such as pumpable food systems and beverage lines, etc. Food service wares can also be disinfected with the composition of the invention. The composition is also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity.

A method of sanitizing substantially fixed in-place process facilities comprises the following steps. The use composition of the invention is introduced into the process facilities at a temperature in the range of about 4° to 60° C. After introduction of the use solution, the solution is circulated throughout the system for a time sufficient to sanitize the process facilities (i.e., to kill undesirable microorganisms). After the system has been sanitized by means of the present composition, the use solution is drained from the system. Upon completion of the sanitizing step, the system optionally may be rinsed with other materials such as potable water. The composition is preferably circulated through the process facilities for 10 minutes or less.

The composition may also be employed by dipping food processing equipment into the use solution, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use composition is contacted with any of the above contaminated surfaces or items at use temperatures in the range of about 4° to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric. As the term "sanitizing" is used in the method of the instant invention, it means a reduction in the population numbers of undesirable microorganisms by about 5 powers of 10 or greater (i.e., at least 5 orders of magnitude) after a 30 second exposure time. It is to be emphasized that the instant use solution provides cleaning as well as sanitizing performance although its primary utility is sanitizing. The composition may also be used to achieve disinfection or sterilization (i.e., elimination of all microorganisms) by employing higher levels of peracids in the use solution.

The following Examples are intended to illustrate the above invention and should not be construed as to narrow its scope. One skilled in the art will readily recognize that these Examples suggest many other ways in which the present invention could be practiced.

EXAMPLE 1

Experiments were conducted to determine the antimicrobial efficacy of pure peroxyacids. Table I below demonstrates the antimicrobial efficacy of pure peroxyacids at very low levels when exposed to S. aureus and E. coli. The peroxyacids listed in Table I were tested by diluting them in 0.05M citrate buffer made in distilled water and were exposed to the bacteria for 30 seconds at 20° C. As Table I indicates, the diperoxyacids were somewhat less active than the peroxyfatty acids. Peroxydecanoic acid was very effective at very low levels against S. aureus, but higher levels were required to be effective against E. coli. Higher levels were also required at pH 5.

TABLE I

Comparison of Cidal Activity of Peroxyacids

| Peroxyacid | pH | Minimum concentration required for 5-log reduction (ppm)[a] | |
|---|---|---|---|
| | | S. aureus | E. coli |
| Peroxyhexanoic ($C_6$) | 3.5 | 15 | 15 |
| | 5.0 | 20 | 15 |
| Diperoxyadipic ($C_6$) | 3.5 | >50 | 40 |
| | 5.0 | >60 | 35 |
| Peroxyoctanoic ($C_8$) | 3.5 | 5 | 5 |
| | 5.0 | 10 | 15 |
| Peroxydecanoic ($C_{10}$) | 3.5 | 3 | 10 |
| | 5.0 | 1 | 30 |
| Diperoxysebacic ($C_{10}$) | 3.5 | 15 | 15 |
| | 5.0 | 10 | 50 |

[a]Peroxyacids tested at 5-ppm increments, or at 1, 3, and 5 ppm where appropriate.

In Table II below, the antimicrobial synergism between the $C_2$ and $C_3$ peroxyacids when combined with $C_8$ and $C_{10}$ peroxyfatty acids is shown. As Table II shows, there was little or no antimicrobial activity when the $C_2$ and $C_3$ peroxyacids and the $C_8$ and $C_{10}$ peroxyfatty acids were tested alone. However, when a $C_2$ or $C_3$ peroxyacid was combined with a $C_8$ or $C_{10}$ peroxyfatty acid, the bacterial kill of E. coli multiplied exponentially. These tests were conducted at pH 4.5 or 5, the pH at which E. coli is more difficult to kill (see Table II).

TABLE II

Synergistic Interaction of Peroxyacids

| $C_2$ [Peroxyacetic] (ppm) | $C_3$ [Peroxypropionic] (ppm) | $C_8$ [Peroxyoctanoic] (ppm) | $C_{10}$ [Peroxydecanoic] (ppm) | Log reduction |
|---|---|---|---|---|
| 25 | | 0 | | 0[a] |
| 0 | | 5 | | 0.1[a] |
| 25 | | 5 | | 3.8[a] |
| | 25 | 0 | | 0.3[b] |
| | 0 | 6 | | 0.1[b] |

TABLE II-continued

Synergistic Interaction of Peroxyacids

| $C_2$ [Peroxyacetic] (ppm) | $C_3$ [Peroxypropionic] (ppm) | $C_8$ [Peroxyoctanoic] (ppm) | $C_{10}$ [Peroxydecanoic] (ppm) | Log reduction |
|---|---|---|---|---|
|  | 25 | 6 |  | 3.9[b] |
| 30 |  |  | 0 | 0.7[a] |
| 0 |  |  | 6 | 0[a] |
| 30 |  |  | 6 | 2.6[a] |

[a] *E. coli*, pH 5, distilled water
[b] *E. coli*, pH 4.5, 500 ppm hard water

EXAMPLE 2

A mixture of short chain fatty acids commercially available from Emery Corporation under the designation "EMERY 658" was employed in producing a sanitizing concentrate composition of the present invention. The "EMERY 658" acid is a mixture of caprylic acid ($C_8$) and capric acid ($C_{10}$). The perfatty acids were prepared by the method of Parker, et al., *J. Amer. Chem. Soc.*, 77, 4037 (1955) which is incorporated by reference. The perfatty acid component (also containing 34% acetic acid and 10% hydrogen peroxide) was combined with a pre-made solution of 10.42% peracetic acid, a separate amount of acetic acid, water, and an n-octanesulfonate hydrotrope coupler (NAS 8D). The final composition of this Example was as listed in Table III.

EXAMPLE 3

A second composition of the present invention was prepared as described in Example 2, except that caprylic acid ($C_8$) and capric acid ($C_{10}$) replaced some of the perfatty acid of Example 2. The concentration of peracetic acid was 5% while the concentration of perfatty acids was reduced to 1.5% (See Table III).

EXAMPLE 4

The composition of Example 4 was prepared according to the procedure of Example 2, except that no peracetic acid or hydrogen peroxide was added to the composition. The acetic acid component was increased to 39 wt-% and the composition contained 5% perfatty acid (see Table III). Also, a chelating agent (Dequest 2010) was added to the composition.

EXAMPLE 5

The composition of Example 5 was prepared the same as Example 4 except that caprylic acid and capric acid were added to the composition in addition to the percaprylic and percapric acid of Example 4. The composition contained 3.5% fatty acid and 1.5% perfatty acid (see Table III).

EXAMPLE 6

Example 6 was prepared with only peracetic acid, acetic acid, hydrogen peroxide, and water. No perfatty acids or fatty acids were added to the composition of Example 6. The concentration of total peracid was about 5% and the acetic acid concentration was about 39% (see Table III).

EXAMPLE 7

Example 7 was prepared the same as Example 5 except that no peracids were employed, only a mixture of fatty acids and acetic acid was used, along with water, NAS 8D, and Dequest 2010. The composition contained 5% fatty acid (see Table III).

TABLE III

| Ingredient | Wt-% of Ingredients | | | | | |
|---|---|---|---|---|---|---|
|  | Ex. 2 | Ex. 3 | Ex. 4 | Ex. 5 | Ex. 6 | Ex. 7 |
| Peracetic Acid (10.42% solution, 34% acetic acid, 10% $H_2O_2$) | 50 | 50 | — | — | 50 | — |
| Acetic Acid | 22 | 22 | 39 | 39 | 22 | 39 |
| Percaprylic Acid ($C_8$) | 3.75 | 1.125 | 3.75 | 1.125 | — | — |
| Percapric Acid ($C_{10}$) | 1.25 | 0.375 | 1.25 | 0.375 | — | — |
| Caprylic Acid ($C_8$) | — | 2.625 | — | 2.625 | — | 3.75 |
| Capric Acid ($C_{10}$) | — | 0.875 | — | 0.875 | — | 1.25 |
| NAS 8D | 10 | 10 | 10 | 10 | — | 10 |
| Water | 13 | 13 | 45 | 45 | 28 | 45 |
| Dequest 2010 | — | — | 1 | 1 | — | 1 |

Antimicrobial Efficacy of Examples 2–7

The compositions prepared according to Examples 2–7 were tested for their antimicrobial efficacy using the testing procedure of the standard A.O.A.C. sanitizing test. All of the samples tested of Examples 2–7 were made about 1 hour prior to testing. The bacteria used in the test procedure were *S. aureus* and *E. coli*. Distilled water was used to dilute the concentrate compositions of Examples 2–7 and the composition was employed at room temperature. The following neutralizers were employed in the test: 0.1% thiosulfate, peptone, 0.5% $K_2HPO_4$, 0.025% catalase for peracetic acid; chambers for fatty acid; 0.1% thiosulfate, peptone, 0.025% catalase for peracetic acid/fatty acid (perfatty acid).

The antimicrobial activity of Examples 2–7 are summarized in Table IV. Examples 2 and 3 were tested using four samples (a,b,c,d) and Examples 4–7 were tested using two samples (a,b). As can be seen in Table IV, Examples 2–5 exhibited excellent kill (>log 6) of both *S. aureus* and *E. coli* at 50 ppm of peracid. Examples 6 and 7 (containing no perfatty acids) exhibited little or no activity. More specifically, Example 2 was tested at 1,000 and 500 ppm total product (50 and 25 ppm of both peroxyacetic acid and perfatty acid). At these low concentrations, the peracid combination gave a 6–7 log reduction in the bacterial count. Example 3 was tested at 1,000 and 500 ppm total product, and also had a 6–7 log reduction in the bacterial count. At the 500 ppm product concentration the product corresponds to 25 ppm of peroxyacetic acid and 7.5 ppm of perfatty acids. Example 4, at 1,000 ppm of total product (50 ppm of perfatty acid), completely killed all bacteria (greater than 7 log reduction). Example 5 also resulted in a complete kill using 1,000 ppm of total product (15 ppm perfatty acid). Example 6 contained no perfatty acid (only 50 ppm of peroxyacetic acid) and showed no activity against *S. aureus* and poor activity against *E. coli*. This is due to the fact that peroxyacetic acid is generally not effective at this level, and is generally used at concentrations greater than 100 ppm. Example 7, containing 5% fatty acid (30 ppm) and no perfatty acid at 1,000 ppm total product showed no activity toward either organism.

TABLE IV

| Ex. | Sample | Test Product Concentration (ppm) | POAA[1]/POFA[2]/FA[3] Concentration (ppm) | pH | Log₁₀ Kill S. aureus | Log₁₀ Kill E. coli |
|---|---|---|---|---|---|---|
| 2 | a | 1000 | 50/50/0 | 3.5 | 6.13 | >7.30 |
|   | b | 1000 | 50/50/0 | 3.5 | 6.52 | 7.30 |
|   | c | 500 | 25/25/0 | 3.68 | 6.63 | 7.00 |
|   | d | 500 | 25/25/0 | 3.68 | 6.78 | 7.30 |
| 3 | a | 1000 | 50/15/35 | 3.52 | 7.18 | 7.30 |
|   | b | 1000 | 50/15/35 | 3.52 | 6.63 | 6.90 |
|   | c | 500 | 25/7.5/17.5 | 3.68 | 6.70 | 6.76 |
|   | d | 500 | 25/7.5/17.5 | 3.68 | 7.18 | 7.00 |
| 4 | a | 1000 | 0/50/0 | 3.5 | >7.18 | >7.30 |
|   | b | 1000 | 0/50/0 | 3.5 | >7.18 | >7.30 |
| 5 | a | 1000 | 0/15/35 | 3.5 | >7.18 | >7.30 |
|   | b | 1000 | 0/15/35 | 3.5 | >7.18 | >7.30 |
| 6 | a | 1000 | 50/0/0 | 3.49 | NMA[4] | 3.48 |
|   | b | 1000 | 50/0/0 | 3.49 | NMA | 3.80 |
| 7 | a | 1000 | 0/0/30 | 3.46 | NMA | NMA |
|   | b | 1000 | 0/0/30 | 3.46 | NMA | NMA |

[1]POAA = Peroxyacetic Acid
[2]POFA = Peroxyfatty Acid
[3]FA = Fatty Acid
[4]NMA = No measurable activity

EXAMPLEs 8–11

Examples 8–11 were prepared by substantially the same procedure as the previous Examples, except that hydrogen peroxide ($H_2O_2$) was mixed with acetic acid and $C_8$–$C_{10}$ fatty acids (Emery 658) to make the peracids of the composition. Table V summarizes the components and amounts of the various compositions of Examples 8–11 which were made.

TABLE V

Peracid Test Formulations

| Ingredient | Ex. 8 | Ex. 9 | Ex. 10 | Ex. 11 |
|---|---|---|---|---|
| Acetic Acid | 44 | 39 | 34 | 49 |
| H₂O₂ (35%) | 40 | 40 | 40 | 40 |
| Dequest 2010 | 1 | 1 | 1 | 1 |
| NAS 8D | 10 | 10 | 10 | 10 |
| Emery 658 | 5 | 10 | 15 | — |

Peracid Stability, Cidal Activity of Examples 8–11

Each of Examples 8–11 were tested for peracid stability and cidal activity using the A.O.A.C. sanitizing test against S. aureus and E. coli at room temperature with the formulations diluted in distilled water. Tables VI–IX show the cidal activity of each formulation. Generally all of the formulations reached maximum peracid formation within about 12 days. All of the formulations obtained about 2.5% peracid except Example 10 (15% fatty acid) which obtained about 11.5% peracid. Table VI summarizes the cidal activity of Example 8 in which the composition was measured for cidal activity on the first day up to day 33. At 250 ppm of total product, there were about 4–5 ppm of perfatty acid and about 20 ppm of peracetic acid as determined by carbon 13 NMR spectroscopy. The results are summarized in Table VI.

TABLE VI

Peracid Stability, Cidal Activity of Example 8

| Day | Peracid Percent | Test[a] Concentration | Test pH | Ave. Log Reduction S. aureus | Ave. Log Reduction E. coli |
|---|---|---|---|---|---|
| 1 | 4.28 | 250 ppm | 3.92 | 6.28 | NMA[b] |
| 6 | 11.00 | 250 ppm | 3.91 | >7.38 | >7.18 |
| 8 | 11.08 | 250 ppm | 3.86 | >7.11 | >7.12 |
| 12 | 12.43 | 250 ppm | 3.83 | >7.18 | 6.96 |
| 15 | 12.74 | 250 ppm | 3.88 | 6.83 | — |
| 33 | 10.18 | 250 ppm | 3.83 | 5.18 | 6.34 |

[a]ppm total product
[b]No measurable activity

The cidal activity of Example 9 is summarized in Table VII below. The peracetic acid concentration at 250 ppm of product was about 20–21 ppm and the concentration of perfatty acid was about 11 ppm. The concentration of peracetic acid at 50 ppm of product was about 4 ppm and the concentration of perfatty acid was about 2 ppm.

TABLE VII

Peracid Stability, Cidal Activity of Example 9

| Day | Peracid Percent | Test[a] Concentration | Test pH | Ave. Log Reduction S. aureus | Ave. Log Reduction E. coli |
|---|---|---|---|---|---|
| 1 | 4.88 | 250 ppm | 3.95 | >7.60 | NMA[b] |
| 6 | 10.62 | 250 ppm | 3.92 | >7.38 | >7.18 |
| 8 | 11.61 | 250 ppm | 3.98 | >7.11 | >7.12 |
| 12 | 12.47 | 250 ppm | 3.91 | >7.18 | >7.23 |
| 15 | 12.00 | 250 ppm | 3.95 | 6.95 | — |
|   |   | 120 ppm | 4.18 | >7.13 | — |
|   |   | 50 ppm | 4.41 | 6.39 | — |
| 33 | 10.49 | 250 ppm | 3.85 | 5.20 | 6.22 |

[a]ppm total product
[b]No measurable activity

The cidal activity of Example 10 is summarized in Table VIII below. At 250 ppm of product the peracetic acid concentration was about 19 ppm and the perfatty acid concentration was about 14 ppm.

TABLE VIII

Peracid Stability, Cidal Activity of Example 10

| Day | Peracid Percent | Test[a] Concentration | Test pH | Ave. Log Reduction S. aureus | Ave. Log Reduction E. coli |
|---|---|---|---|---|---|
| 1 | 4.84 | 250 ppm | 3.90 | >7.60 | NMA[b], 4.04 |
| 6 | 9.81 | 250 ppm | 3.96 | >7.38 | >7.18 |
| 8 | 10.99 | 250 ppm | 3.96 | >7.11 | >7.12 |
| 12 | 11.47 | 250 ppm | 3.94 | >7.18 | >7.23 |
| 15 | 11.48 | 250 ppm | 3.96 | 6.83 | — |
| 33 | 10.49 | 250 ppm | 3.95 | 5.25 | 6.53 |

[a]ppm total product
[b]No measurable activity

The cidal activity of Example 11 is summarized in Table IX below. At 250 ppm of product there was about 27 ppm of peracetic acid. At 1000 ppm of product there was about 108 ppm of peracetic acid. No fatty acid was employed in the composition of Example 11.

TABLE IX

Cidal Activity of Example 11

| Day | Peracid Percent | Test(a) Concentration | Test pH | Ave. Log Reduction S. aureus | E. coli |
|---|---|---|---|---|---|
| 5 | 10.95 | 250 ppm | 3.90 | NMA(b) | NMA |
| 7 | 12.03 | 1000 ppm | 3.50 | 4.60 | >7.12 |
| 11 | 12.44 | 1000 ppm | 3.49 | 6.38 | 6.64 |
| 14 | 12.53 | 1000 ppm | 3.50 | 4.17 | — |
| 32 | 10.77 | 1000 ppm | 3.45 | 4.77 | 6.44 |

(a)ppm total product
(b)No measurable activity

When comparing the formulations containing fatty acid (Tables VI–VIII), poor activity was measured against E. coli one day after being formulated. Since the total peracid values were low, more fatty acid was present and gram negative bacteria tend to be less sensitive than gram positive bacteria to the $C_8$–$C_{10}$ fatty acids. However, as more peracid developed over the days indicated, increased cidal activity against E. coli was observed. Table IX indicates that to obtain acceptable activity (greater than or equal to 5 log reduction) using only peracetic acid, the peracetic acid must be tested over 100 ppm active. Secondly, this oxidizing compound is more effective against E. coli than S. aureus.

Generally all the formulations containing fatty acid remain stable after about 1 month. This was confirmed by repeated testing over time at 250 ppm total product for each formulation in which greater than 5 log reductions were measured against S. aureus and E. coli.

EXAMPLEs 12–17

The cidal activity of a two-component system containing both peracetic acid and fatty acid was investigated using the A.O.A.C. sanitizing test. Table X shows the product formulations examined. The test samples include controls showing cidal activity of NAS 8D as well as fatty acid kill against S. aureus. All the samples were tested in distilled water.

TABLE X

| | Wt-% Ingredient | | | | | |
|---|---|---|---|---|---|---|
| Ingredient | Ex. 12 | Ex. 13 | Ex. 14 | Ex. 15 | Ex. 16 | Ex. 17 |
| Base 1(a) | 80 | 80 | 80 | 80 | — | — |
| Base 2(b) | — | — | — | — | 80 | 80 |
| NAS 8D | 10 | — | 10 | 10 | 10 | 10 |
| Octanoic Acid | — | — | 10 | — | — | 10 |
| Emery 658 | — | — | — | 10 | 10 | — |
| $H_2O$ | 10 | 20 | — | — | — | — |

(a)$H_2O_2$, 35%; acetic acid, 35%; Dequest 2010, 1%; $H_3PO_4$ (85%), 29%.
(b)Acetic acid, 35%; Dequest 2010, 1%; $H_3PO_4$ (85%), 29%; $H_2O$, 35%.

Table XI shows the activity measurement of each of Examples 12–17 at various test concentrations. When testing the peracetic acid formulation of Examples 12 and 13 (having no fatty acid), biocidal activity occurred only at 100 ppm or greater. Cidal activity (greater than 4 log reduction) was measured at a minimal concentration of 10 ppm peracid with fatty acid in the system (Example 14). At 10 ppm peracid, the composition containing Emery 658 (Example 15) had better activity than the system containing only $C_8$ (octanoic) fatty acid (Example 14). In the fatty acid controls (Examples 16 and 17), the Emery 658 had more cidal activity than the $C_8$ fatty acid. At total product test concentrations equivalent to 10 or 25 ppm peracid, the fatty acid in the system of Example 16 did not have significant cidal activity. Example 17 did not have significant cidal activity at any test concentration.

TABLE XI

Peracid Cidal Activity Against S. aureus

| Example | Peracid (%) | Concentration (ppm Peracid) | Test pH | Log(a) Reduction |
|---|---|---|---|---|
| 12 | 7.02 | 50 | 2.79 | NMA(b) |
| | | 100 | 2.54 | 5.45 |
| | | 150 | 2.41 | >7.70 |
| 13 | 6.25 | 50 | 2.76 | NMA |
| | | 100 | 2.52 | 4.51 |
| | | 150 | 2.40 | 5.84 |
| 14 | 9.32 | 10 | 3.52 | 4.22 |
| | | 25 | 3.16 | >7.70 |
| | | 50 | 2.90 | >7.70 |
| 15 | 9.73 | 10 | 3.50 | 6.82 |
| | | 25 | 3.19 | 7.55 |
| | | 50 | 2.88 | >7.70 |
| 16 | — | —(c) | 3.53 | 0.70 |
| | | —(c-1) | 3.18 | 1.04 |
| | | —(c-2) | 2.88 | 4.07 |
| 17 | — | —(d) | 3.51 | 0.93 |
| | | —(d-1) | — | 0.66 |
| | | —(d-2) | — | 0.97 |

(a)Average of duplicate testing.
(b)No measurable activity.
(c)Same total product concentration as Example 15 @ 10 ppm peracid (about 100 ppm product).
(c-1)Same total product concentration as Example 15 @ 25 ppm peracid (about 250 ppm product).
(c-2)Same total product concentration as Example 15 @ 50 ppm peracid (about 500 ppm product).
(d)Same total product concentration as Example 14 @ 10 ppm peracid (about 100 ppm product).
(d-1)Same total product concentration as Example 14 @ 25 ppm peracid (about 250 ppm product).
(d-2)Same total product concentration as Example 14 @ 50 ppm peracid (about 500 ppm product).

The cidal activity of a peracetic acid/fatty acid system was measured comparing freshly made formulations to month-old formulations of Examples 14 and 15. These formulations are shown in Table XII which compares the titration values of month-old formulations to the same freshly prepared. Table XIII shows the cidal activity of month-old and fresh formulations of Examples 14 and 15.

TABLE XII

Peracid Titration Values

| | Ex. 14 | Ex. 15 | Ex. 14 | Ex. 15 |
|---|---|---|---|---|
| Date formulated | Month-Old | Month-Old | Fresh | Fresh |
| % $H_2O_2$ | 2.15 | 2.07 | 1.99 | 1.99 |
| % Peracid | 5.37 | 5.35 | 4.85 | 4.86 |
| % Total $O_2$ | 2.14 | 2.10 | 1.96 | 1.96 |

TABLE XIII

Peracid Cidal Activity Against S. aureus

| Example | Peracid (%) | Test Concentration (ppm Peracid) | Test Reduction | Log(a) |
|---|---|---|---|---|
| 14 (Month-Old) | 5.37 | 10 | 3.46 | NMA(b) |
| | | 25 | 3.07 | >7.48 |
| 14 (Fresh) | 4.85 | 10 | 3.34 | 5.07 |
| | | 25 | 2.97 | 7.30 |
| 15 (Month-Old) | 5.35 | 10 | 3.52 | 5.29 |
| | | 25 | 3.04 | 7.24 |

TABLE XIII-continued

Peracid Cidal Activity Against *S. aureus*

| Example | Peracid (%) | Test Concentration (ppm Peracid) | Test Reduction | Log(a) |
|---|---|---|---|---|
| 15 | 4.86 | 10 | 3.42 | NMA[c]/3.68 |
| (Fresh) | | 25 | 2.99 | 7.48 |

[a] Average of duplicate testing.
[b] No measurable activity.
[c] Duplicate testing in which only one sample exhibited cidal activity.

As can be seen from Table XIII, cidal activity in the peracetic acid/fatty acid system occurs at test concentrations as low as 10 or 25 ppm peracid. Mixed results occurred at 10 ppm peracid between the month-old and fresh formulations of Examples 14 and 15, however, increasing the concentration to 25 ppm resulted in a uniform kill activity (>7 log reduction).

An additional test was run to determine how quickly compounds exhibiting cidal activity are formed upon adding fatty acid to a peracetic acid system. Examples 12, 15 and 16 were tested. Examples 12 and 15 were formulated the day before testing and were day-old samples. Another test sample of Example 15 was formulated immediately prior to testing. Example 16 containing Base 2 (no $H_2O_2$) was used to show cidal activity from the fatty acid at low test concentrations. Table XIV shows the cidal activity of each Example in distilled water against *S. aureus*.

TABLE XIV

Cidal Activity Against *S. aureus*

| Example | Age | ppm Peracid | Test PH | Log[a] Reduction |
|---|---|---|---|---|
| 12 | 1 day | 50 | 2.94 | NMA[b] |
|  |  | 100 | 2.71 | 6.60 |
| 15 | 1 day | 10 | 3.68 | 7.02 |
|  |  | 25 | 3.35 | >7.20 |
| 15 | fresh | 10 | 3.76 | NMA |
|  |  | 25 | 3.32 | NMA |
| 16 | 22 days | —[c] | 3.74 | NMA |
|  |  | —[d] | — | NMA |

[a] Average of duplicate testing.
[b] No measurable activity.
[c] Equivalent total product concentration as Example 15 (day old) @ 10 ppm peracid.
[d] Equivalent total product concentration as Example 15 (day old) @ 25 ppm peracid.

The data from Table XIV suggests that the formation of compounds containing cidal activity when adding fatty acid to a peracetic acid system is not immediate, but does occur within a day. The formation of compounds exhibiting cidal activity occurred within a day after adding fatty acid to the peracetic acid system as in Example 15 with cidal activity occurring at a concentration as low as 10 ppm peracid. Thus, the cidal activity is not due to the mere combination of fatty acid and peroxyacetic acid, but the fatty acid must be converted to the perfatty acid before substantially enhanced cidal activity occurs.

EXAMPLES 18–22

A two-component system containing peracetic acid and perfatty acid was formulated and tested to determine its sanitizing activity over just a peracetic acid system. Table XV shows premixes 1 and 2 used in making the composition. The premixes were both made with $H_2O_2$ (35% solution), acetic acid, Dequest 2010, and with/without $H_3PO4$. Premix 1 was made about 5 months before premix 2. To each premix was added NAS 8D, a $C_8$ fatty acid or Emery 658 as shown in Table XVI to complete the formulation of Examples 18–21. Example 22 was formulated as a control and had no fatty acid.

TABLE XV

Peracid Premixes

| | Wt-% Component | |
|---|---|---|
| Component | Premix 1 | Premix 2 |
| $H_2O_2$ (35%) | 75.0 | 35.0 |
| Acetic acid (glacial) | 24.0 | 35.0 |
| Dequest 2010 | 1.0 | 1.0 |
| $H_3PO_4$ (85%) | — | 29.0 |

TABLE XVI

Perfatty Acid/Peracetic Acid Formulations

| | Wt-% Ingredient | | | | |
|---|---|---|---|---|---|
| Ingredient | Ex. 18 | Ex. 19 | Ex. 20 | Ex. 21 | (Control) Ex. 22 |
| Premix 1 | 80.0 | — | 80.0 | — | — |
| Premix 2 | — | 80.0 | — | 80.0 | — |
| NAS 8D | 10.0 | 10.0 | 10.0 | 10.0 | — |
| $C_8$ Fatty Acid | 10.0 | 10.0 | — | — | — |
| Emery 658 | — | — | 10.0 | 10.0 | — |
| Acetic Acid (Glacial) | — | — | — | — | 24.0 |
| $H_2O_2$ (35%) | — | — | — | — | 75.0 |
| Dequest 2010 | — | — | — | — | 1.0 |

Table XVII shows the sanitizing activity measured from each formulation of Examples 18–22 at 50, 100, or 150 ppm peracetic acid against *S. aureus*.

TABLE XVII

Sanitizing Efficacy of Perfatty Acid/Peracetic Acid System vs. Sanitizing Efficacy of Peracetic Acid System

| Example | Total Peracid[a] (Percent) | Fatty Acid (Percent) | Test Concentration (ppm) | Test pH | Log[b] Reduction |
|---|---|---|---|---|---|
| 18 | 7.69 | 10.0 | 150 | 3.53 | >7.06 |
|  |  |  | 100 | 3.64 | >7.06 |
|  |  |  | 50 | 3.83 | >7.06 |
| 19 | 11.21 | 10.0 | 150 | 2.71 | >7.06 |
|  |  |  | 100 | 2.80 | >7.06 |
|  |  |  | 50 | 3.08 | >7.06 |
| 20 | 9.08 | 10.0 | 150 | 3.64 | >7.06 |
|  |  |  | 100 | 3.65 | >7.06 |
|  |  |  | 50 | 3.85 | >7.06 |
| 21 | 10.92 | 10.0 | 150 | 2.68 | >7.06 |
|  |  |  | 100 | 2.77 | >7.06 |
|  |  |  | 50 | 3.10 | >7.06 |
| 22 (Control) | 10.40 | — | 150 | 3.56 | 7.06 |
|  |  |  | 100 | 3.68 | 3.89 |
|  |  |  | 50 | 3.93 | NMA[c] |

[a] As peracetic acid
[b] Average of duplicate testing against *S. aureus*.
[c] No measurable activity.

Extremely good kill (>7 log reduction) was obtained with or without $H_3PO_4$ in the perfatty acid formulations of Examples 18–21. The two component system of $C_8$ fatty acid or Emery 658 in combination with peracetic acid (Examples 18–21) had significantly better kill than the peracetic acid system alone (Example 22) at a test concentration of 50 to 100 ppm. No activity was measured at 50 ppm with the single peracetic acid system of Example 22.

EXAMPLEs 23–26

The effect of alkyl chain length on antimicrobial efficacy of perfatty acids was determined for percaprylic ($C_8$) acid, percapric ($C_{10}$) acid and a percaprylic/percapric (3:1) perfatty acid mixture using the compositions of Examples 23–26 summarized in Table XVIII below.

TABLE XVIII

| Ingredient | Wt-% of Ingredient | | | |
|---|---|---|---|---|
| | Ex. 23 | Ex. 24 | Ex. 25 | Ex. 26 |
| Percaprylic ($C_8$) Acid | 1 | — | — | — |
| Percapric ($C_{10}$) Acid | — | 1 | — | — |
| $C_8 + C_{10}$ (3:1) Perfatty Acid | — | — | 1 | — |
| Acetic Acid | 10 | 10 | 10 | 10 |
| Water | 84 | 84 | 84 | 85 |
| NAS 8D | 5 | 5 | 5 | 5 |

The antimicrobial efficacy of Examples 23–26 are summarized in Table XIX below. Examples 23–25 were tested using three samples (a, b, c) of 5, 10, and 15 ppm of perfatty acid respectively. Example 26, containing no perfatty acid, was diluted to an equivalent formulation of Examples 23–25 containing perfatty acid. As can be seen from Table XIX, significant kill occurred at 5 ppm for *S. aureus* using Examples 23–25. Significant kill occurred against *E. coli* at 10 ppm of perfatty acid in Examples 23–25. Example 26 (having no perfatty acid) did not produce any kill of either microorganism.

TABLE XIX

Antimicrobial Efficacy of Examples 23–26

| Example | Sample | Perfatty Acid Concentration (ppm) | Log Kill | |
|---|---|---|---|---|
| | | | *S. aureus* | *E. coli* |
| 23 | a | 5 | >7.0 | 3.6 |
| | b | 10 | — | >7.2 |
| | c | 15 | — | >7.2 |
| 24 | a | 5 | >7.0 | 3.0 |
| | b | 10 | — | >7.2 |
| | c | 15 | — | >7.2 |
| 25 | a | 5 | >7.0 | <3.0 |
| | b | 10 | — | >7.2, 5.5 |
| | c | 15 | — | >7.2 |
| 26 | a | —ᵃ | 0 | — |
| | b | —ᵇ | — | 0 |

ᵃEquivalent total product concentration as Examples 23, 24, 25 at 5 ppm perfatty acid.
ᵇEquivalent total product concentration as Examples 23, 24, 25 at 15 ppm perfatty acid.

EXAMPLE 27

The antimicrobial activity of percaprylic acid against *E. coli* was measured at a 30 second exposure at varying pH's. The formulation contained 94% water, 5% NAS 8D, and 1% percaprylic acid. The formulation was diluted in a buffer of 0.05M citrate and 0.05M potassium phosphate. The log kill of this formulation at increasing pH's is summarized in Table XX. Samples containing 7 ppm and 25 ppm of percaprylic acid were tested. As Table XX indicates, significant kill at 7 ppm occurred at a pH of 3.0. Significant kill levels were maintained at 25 ppm through a pH of 7.0.

TABLE XX

Antimicrobial Efficacy of Percaprylic Acid against *E. coli*

| pH | Log Kill (Perfatty Concentration 7 ppm) | Log Kill (Perfatty Concentration 25 ppm) |
|---|---|---|
| 3.0 | >7.2 | >7.2 |
| 5.0 | <3.0 | >7.2 |
| 7.0 | <3.0 | >7.2 |
| 8.9 | — | <3.0 |
| 9.0 | <3.0 | — |

EXAMPLES 28–36

The compositions of Examples 28–30 were made to determine the limitations on cidal activity of compositions containing at least 30% acetic acid. Higher acetic acid formulations were also tested for their cidal activity. The composition of Example 30 was prepared with no coupler (NAS 8D). The compositional ingredients of Examples 28–30 are summarized below in Table XXI.

TABLE XXI

| Ingredient | Wt-% of Ingredient | | |
|---|---|---|---|
| | Example 28 | Example 29 | Example 30 |
| Acetic Acid | 30.0 | 50.0 | 50.0 |
| $H_2O_2$ (35%) | 30.0 | 15.0 | 15.0 |
| Dequest 2010 | 1.0 | 1.0 | 1.0 |
| $C_8$ Fatty Acid | 4.0 | 6.0 | 5.0 |
| NAS 8D (Spray Dried) | 5.0 | 5.0 | — |
| Distilled Water | 30.0 | 23.0 | 29.0 |

The antimicrobial efficacy of Examples 28–30 was determined using the procedure of the standard A.O.A.C. sanitizing test. The compositions of Examples 28–30 were diluted with 500 ppm hard water and employed at 25° C. The bacteria used in the test procedure were *S. aureus* and *E. coli*, and a TGE plating medium was employed. Exposure time of the compositions to the bacteria was 30 seconds. The neutralizer employed in the testing procedure contained 0.1% thiosulfate, 1.0% peptone, and 0.025% catalase. The antimicrobial activity of Examples 28–30 is summarized in Table XXII below.

TABLE XXII

Cidal Activity of Examples 28–30

| Formulation | Concentration | pH | Log Reduction | |
|---|---|---|---|---|
| | | | *S. aureus* | *E. coli* |
| Example 28 | 1 oz: 8 gal.ᵃ | 4.48 | >7.15 | >6.89 |
| | 1 oz: 10 gal.ᵇ | 4.83 | >7.15 | >6.89 |
| | 1 oz: 12 gal.ᶜ | 5.04 | >7.15 | 6.41 |
| | 1 oz: 14 gal.ᵈ | 5.52 | >7.15 | 5.76 |
| | 1 oz: 16 gal.ᵉ | 5.94 | >7.15 | 2.95 |

TABLE XXII-continued

Cidal Activity of Examples 28-30

| | | | Log Reduction | |
|---|---|---|---|---|
| Formulation | Concentration | pH | S. aureus | E. coli |
| Example 29 | 40 ppm Active | 4.16 | >7.15 | >6.89 |
| Example 30 | 40 ppm Active | 4.04 | >7.15 | >6.89 | a 54.2 ppm peracid
b 43.3 ppm peracid
c 36.1 ppm peracid
d 31.0 ppm peracid
e 27.2 ppm peracid As Table XXII indicates, very low concentrations of combinations of peroxyacetic acid and peroxyfatty acid are very effective in killing bacteria. Also, Example 30 showed that the composition of the invention is antimicrobially effective without a hydrotrope coupler.

The foregoing discussion and Examples are illustrative of the invention. However, since many embodiments of the invention can be made without departing from the spirit and scope of the invention, the invention resides wholly in the claims hereinafter appended.

I claim:

1. An aqueous peroxyacid antimicrobial composition consisting essentially of:

(a) at least about 10 parts per million (ppm) of a $C_1$–$C_4$ peroxycarboxylic acid; and (b) at least about 1 ppm of an aliphatic $C_6$–$C_{18}$ peroxycarboxylic acid; wherein the aqueous composition has a pH in the range of about 2 to 8.

2. The aqueous composition of claim 1 wherein said $C_1$–$C_4$ peroxycarboxylic acid consists of peroxyacetic acid, peroxypropionic acid, peroxysuccinic acid, peroxyglycolic acid, or mixtures thereof.

3. The aqueous composition of claim 1 wherein said $C_6$–$C_{18}$ peroxycarboxylic acid is a linear aliphatic peroxyfatty acid, or an aliphatic monoperoxy- or diperoxydicarboxylic acid.

4. The aqueous composition of claim 3 wherein said peroxyfatty acid has about 8 to 12 carbon atoms per molecule.

5. The aqueous composition of claim 1 wherein said $C_6$–$C_{18}$ peroxycarboxylic acid consists of peroxyoctanoic acid, peroxydecanoic acid, monoperoxy- or diperoxyadipic acid, monoperoxy- or diperoxysebacic acid, peroxybenzoic acid, or mixtures thereof.

6. The aqueous composition of claim 1 wherein the weight ratio of said $C_1$–$C_4$ peroxycarboxylic acid to said $C_6$–$C_{18}$ peroxycarboxylic acid is about 15:1 to 3:1.

7. An aqueous peroxyacid antimicrobial sanitizing composition consisting essentially of:

(a) about 10 to 75 parts per million (ppm) of a $C_1$–$C_4$ peroxycarboxylic acid;

(b) about 1 to 25 ppm of a peroxyacid of the structure $R_1$—$CO_3H$ wherein R, comprises a linear, saturated hydrocarbon chain having about 5 to 17 carbon atoms;

(c) about 1 to 200 ppm of a hydrotrope coupling agent; and (d) about 2 to 200 ppm of hydrogen peroxide;

wherein the aqueous composition has a pH in the range of about 3 to 7.

8. The aqueous composition of claim 7 wherein said $C_1$–$C_4$ peroxycarboxylic acid consists of peroxyacetic acid, peroxypropionic acid, peroxysuccinic acid, peroxyglycolic acid, or mixtures thereof.

9. The concentrate composition of claim 8 wherein said peroxyacid of (b) is a peroxyfatty acid having about 8 to 12 carbon atoms per molecule.

10. The aqueous composition of claim 9 wherein said peroxyfatty acid consists of peroxyoctanoic acid, peroxydecanoic acid, or mixtures thereof.

11. The aqueous composition of claim 7 wherein said hydrotrope comprises n-octanesulfonate.

12. A method of sanitizing substantially fixed in-place process facilities comprising the steps of:

(a) introducing into the process facilities the composition of claim 1 at a temperature in the range of about 4° C. to 60° C.;

(b) circulating the composition through the process facilities for a time sufficient to sanitize the process facilities; and (c) draining the composition from the process facilities.

13. The method of claim 12 wherein said composition is circulated through the process facilities for about 30 minutes or less.

14. The method of claim 12 wherein after said draining of said composition from the process facilities, the process facilities are rinsed with potable water.

15. The method of claim 12 wherein the process facilities comprise a milk line dairy.

16. The method of claim 12 wherein the process facilities comprise a continuous brewing system.

17. The method of claim 12 wherein the process facilities comprises a pumpable food system or beverage processing line.

18. A method of sanitizing or disinfecting a solid surface or liquid media by bringing the surface or medium into contact with the composition of claim 1 at a temperature in the range of about 4° C. to 60° C. for an effective period of time sufficient to sanitize or disinfect the solid surface or liquid media.

19. A process for sanitizing, disinfecting or sterilizing a contaminated surface using a peroxyacid antimicrobial concentrate composition, comprising the steps of:

(a) diluting in an aqueous liquid said antimicrobial concentrate, thereby forming an aqueous antimicrobial solution, said antimicrobial concentrate consisting essentially of (i) about 0.01 to 25 wt-% of a $C_1$–$C_4$ peroxycarboxylic acid;

(ii) about 0.01 to 10 wt-% of an aliphatic $C_6$–$C_{18}$ peroxycarboxylic acid;

wherein said aqueous antimicrobial solution has a pH of about 2 to 8;

(b) contacting said aqueous antimicrobial solution with said contaminated surface for a period of time effective to sanitize, disinfect, or sterilize said surface.

20. The process of claim 19 wherein said antimicrobial concentrate further consists of about 0.1–30 wt-% of a hydrotrope coupling agent capable of solubilizing said $C_6$–$C_{18}$ peroxycarboxylic acid in the concentrate and when the concentrate is diluted with water.

21. The process of claim 19 wherein said $C_1$–$C_4$ peroxycarboxylic acid consists of peroxyacetic acid, peroxypropionic acid, peroxysuccinic acid, peroxyglycolic acid, or mixtures thereof.

22. The process of claim 19 wherein said $C_6$–$C_{18}$ peroxycarboxylic acid consists of peroxyoctanoic acid, peroxydecanoic acid, monoperoxy- or diperoxyadipic acid, monoperoxy- or diperoxysebacic acid, or mixtures thereof.

23. The process of claim 20 wherein said hydrotrope coupling agent consists of n-octanesulfonate, a xylene sulfonate, a naphthalene sulfonate, or mixtures thereof.

24. The process of claim 19 wherein the contaminated surface is an inanimate solid surface contaminated by a biological fluid comprising blood, other hazardous body fluids, or mixtures thereof.

25. The process of claim 19 wherein the contaminated surface comprises the surface of food service wares or equipment.

26. The process of claim 19 wherein the contaminated surface comprises the surface of a fabric.

27. The composition of claim 1 further consisting of an effective amount of a chelating agent for binding polyvalent metal cations.

28. The composition of claim 27 wherein said chelating agent is 1-hydroxyethylidene-1,1-diphosphonic acid.

29. The composition of claim 7 further comprising an effective amount of a chelating agent for binding polyvalent metal cations.

30. The composition of claim 29 wherein said chelating agent is 1-hydroxyethylidene-1,1-diphosphonic acid.

31. The process of claim 19 wherein said antimicrobial concentrate further consists of an effective amount of a chelating agent for binding polyvalent metal cations.

32. The process of claim 31 wherein said chelating agent is 1-hydroxyethylidene-1,1-diphosphonic acid.

* * * * *

UNITED STATES PATENT AND TRADEMARK OFFICE
CERTIFICATE OF CORRECTION

PATENT NO. : 5,718,910

DATED : February 17, 1998

INVENTOR(S) : Oakes et al.

It is certified that error appears in the above-identified patent and that said Letters Patent is hereby corrected as shown below:

On column 5, line 37, please insert —In— before "this manner"

On column 11, line 59, please delete "2.5%" and replace with —12.5%—

On column 13, line 50, please delete "Emery 658 — — 10 10 — —" and replace with —Emery 658 — — — 10 10 ——

On column 14, lines 60-61, please delete "Test Reduction" and replace with —Test pH—

On column 14, lines 60-61, please delete "Log (a)" and replace with —Log (a) Reduction—

On column 15, lines 5-6, please delete "Test Reduction" and replace with —Test pH—

On column 15, lines 5-6, please delete "Log (a)" and replace with —Log (a) Reduction—

On column 19, line 48, please delete "peroxybenzoic acid"

On column 20, line 3, please delete "concentrate" and replace with —aqueous—

On column 22, line 3, please delete "comprising" and substitute therefore —consisting of—

Signed and Sealed this

Eighth Day of September, 1998

Attest:

BRUCE LEHMAN

*Attesting Officer*  *Commissioner of Patents and Trademarks*